United States Patent [19]

Ashida

[11] Patent Number: 4,568,703
[45] Date of Patent: Feb. 4, 1986

[54] PROCESS FOR THE PRODUCTION OF POLYMERS CONTAINING ISOCYANURATE AND OR OXAZOLIDONE LINKAGES

[75] Inventor: Kaneyoshi Ashida, Detroit, Mich.

[73] Assignee: BP Chemicals Limited, London, England

[21] Appl. No.: 635,351

[22] Filed: Jul. 27, 1984

[51] Int. Cl.$^4$ ............ C08G 18/14; C08G 18/22; C07F 7/28
[52] U.S. Cl. ........................ 521/124; 556/56; 521/902; 528/53; 528/55; 528/73
[58] Field of Search ............... 260/429.5; 521/124, 521/902; 528/53, 55, 73

[56] References Cited

U.S. PATENT DOCUMENTS

| | | | |
|---|---|---|---|
| 3,047,515 | 7/1962 | Piirma | 260/429.5 |
| 3,320,193 | 5/1967 | Beck et al. | 260/429.5 |
| 3,721,689 | 3/1973 | Bardinet | 260/429.5 |
| 3,772,355 | 11/1973 | Merz | 260/429.5 |
| 4,022,721 | 5/1977 | Ashida | 521/124 |
| 4,189,541 | 2/1980 | Ohashi et al. | 521/902 |
| 4,271,273 | 6/1981 | Biranowski et al. | 521/124 |
| 4,365,670 | 12/1982 | McLaughlin | 521/124 |

Primary Examiner—Herbert S. Cockeram
Attorney, Agent, or Firm—Brooks, Haidt, Haffner & Delahunty

[57] ABSTRACT

Titanium compounds of the formula $Ti(OX)_4$ or $Ti(O-R_2)_2NR_3)_2$, where (a) X is selected from the group comprising $-R_1$, $-R_2-OH$, $-(R_2-O)_n-OH$, $-R_2N(R_3)_2$, and $-R_2-N(R_2)(R_3)OH$; (b) $R_1$ is a $C_5-C_8$ alkyl group, $R_2$ is a $C_2-C_4$ alkylene group and $R_3$ is either $-CH_3$ or $-CH_2CH_3$; and (c) $n = 1-20$, are catalysts for the trimerization of isocyanates to isocyanurates and for the formation of 2-oxazolidones from epoxides and isocyanates.

The catalysts may also be used to produce poly(isocyanurates), poly(2-oxazolidones), poly(2-oxazolidone/isocyanurates) and polyurethanes containing isocyanurate and or 2-oxazolidone linkages from the appropriate polyfunctional feedstocks.

11 Claims, No Drawings

PROCESS FOR THE PRODUCTION OF POLYMERS CONTAINING ISOCYANURATE AND OR OXAZOLIDONE LINKAGES

The present invention relates to the production of polymers in which some or all of the linkages between the monomer units which constitute the polymer are isocyanurate groups, oxazolidone groups or a mixture of the two. In particular the invention relates to polymers of the type described above which have been made by reaction of a polyfunctional isocyanate either with itself or with a monomeric polyepoxide, a polyol or a mixture of the two.

The reaction of isocyanates with alcohols to form urethanes is a well known chemical reaction and, in the case where the isocyanate is a polyisocyanate and the alcohol is a polyol, has been industrially exploited on a large scale to form condensation polymers in which the monomeric units are linked by urethane groups, the so called polyurethanes. The reaction typically responsible for producing the linkage is represented by the equation $$RNCO + R^1OH \rightarrow RHNCO_2R^1.$$

Although the reaction between monofunctional isocyanates and monofunctional alcohols are typically selective and lead to formation of the urethane, the use of polyfunctional isocyanates and alcohols can cause side reactions to occur. Thus in the formation of a polyurethane there can occur, in addition to the main urethane linkage forming reaction one or more side reactions which lead to the formation of non-urethane linkages. Such linkages, depending on their concentration in the finished polymer are able to modify the physical properties of the product. In many cases such modifications produce desirable attributes in the finished polymer and consequently it is known to add to the polymerisation mixture catalysts which are specifically able to enhance the rate of such side reactions.

An example of such a side reaction is one which generates isocyanurate linkages. Thus it is known that isocyanates may be trimerised to isocyanurates and that polyisocyanurates can be prepared by oligomerisation of polyfunctional isocyanureates. Hence, by introducing catalysts which specifically catalyse the polyisocyanurate forming reaction into a polyurethane forming reaction mixture polymers containing both urethane and isocyanurate linkages can be formed.

A typical class of catalyst for the ioscyanurate forming reaction are borate esters. Thus U.S. Pat. No. 3,635,848 describes the use of organic borate esters not only to catalyse the formation of polyisocyanurates but also to modify polyurethanes.

Polyisocyanurates have physical properties which make them particularly desirable. Thus in general they are mechanically strong as well as being hydrolysis and temperature resistant. They also have anti smoulder characteristics which make them flame resistant. These desirable feature are also imparted to urethane/isocyanurate polymers. Thus introduction of isocyanurate linkages into polyurethanes tends to enhance mechanical strength, rigidity and resistance to smouldering. Furthermore, by modification of the relative concentrations of isocyanurate and urethane linkages, it is possible to make products which are 'tailor made' to a particular application.

Other catalyst such as tertiary amines and xanthates have also been disclosed in the prior art.

Another important isocyanate reaction is the formation of 2-oxazolindones. It is known, for example, that isocyanates will react with epoxides to produce 2-oxazolidones according to the equation

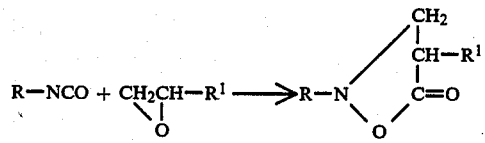

and that poly(2-oxaxolidones), containing exclusively oxazolidone linkages can be prepared from polyfunctional isocyanates and polyfunctional epoxides. Thus, Japanese Pat. No. J80018-726 describes the preparation of such poly(2-oxazolidones) using as catalyst a compound of the formula $$MY_mX_n$$

wherein M is an element of Group IIA, IIIA, IVA, VA, IIB, IVB, VB, VIB, VIIB, VIIIB or a lanthanoid, Y is a neutral ligand and X is halogen $CO_3$, $NO_2$, $ClO_4$, CN or SCN. In the formula m has a value in the range 0–4 and n a value in the range 1–6.

Other catalysts for this reaction have also been described, for example, lithium halides and phosphine oxides, J4 9037–999, organic onium-halide catalysts, U.S. Pat. No. 3,373,406, polysilicic acid, U.S. Pat. No. 4,377,646, and the like.

The poly(2-oxazolidones) produced are useful as foams, coatings, adhesives and the like and have high thermal stability.

A novel class of titanium compounds has now been discovered which is able to catalyst both the trimerisation of isocyanates to form isocyanurates and the reaction of isocyanates with epoxides to form 2-oxazolidones. The catalysts are therefore useful in the preparation of isocyanurates, polyisocyanurates, 2-oxazolidones poly(2-oxazolidones) as well as polyurethanes containing isocyanurate and/or 2-oxaxolidone linkages.

Accordingly therefore the present invention provides titanium compounds characterised in that the compounds are titanates of the formula $$Ti(OX)_4$$

or of the formula

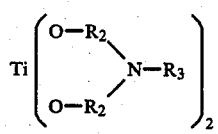

where X is a group selected from

—$R_1$

—$R_2$—OH

—$(R_2—O)_n$—OH

—$R_2N(R_3)_2$

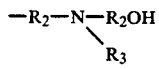

and
R₁=C₅-C₈ alkyl group
R₂=C₂-C₄ alkylene group
R₃=—CH₃ or —C₂H₅
and n=1-20

Typical examples of such catalysts are for example

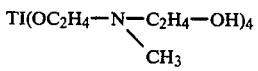

and

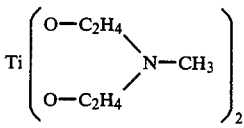

The X groups in each formula can be all identical or can be different.

The novel titanium catalyst described herein are conveniently prepared from a lower alkyl titanate, for example tetrakis (isopropyl) titanate, and the parent alcohol derived from the relevant ester group by transesterification e.g.

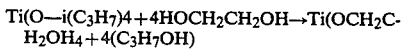

Depending on the nature of the parent alcohol used the final titanate catalyst can range from being a liquid through to highly crystalline solid. Examples of alcohols which can be used are 1-octanol, ethylene glycol, diethylene glycol, 1,2 propanediol, N,N-Dimethylethanolamine methyldiethanolamine and the like. The transesterification reaction can be effected by heating the two reactants together and distilling off the lower alcohol as it is formed.

The titanate esters which form the subject of this invention have two main advantages over the lower titanate esters as catalyst. First the titanates described herein are less sensitive to moisture and hence present fewer problems when manipulated on a large scale. Second, in the case of the trimerisation reaction, the reaction occurs in a more controlled way leading to a more reproducible product.

The novel titanate ester described herein can, as has been mentioned earlier, be used to catalyse the trimerisation of isocyanates to produce isocyanurates. Accordingly, in a first aspect of the invention there is provided a process for the preparation of isocyanurates from one or more isocyanates by reacting the isocyanate or mixture of isocyanates in the presence of an effective amount of the catalyst characterised in that the catalyst is one of the titanate compounds described herein.

An isocyanate or mixture of isocyanates can be used including simple monofunctional alkyl and aryl isocyanates but it is preferred to use polyfunctional isocyanates containing two or more isocyanate groups. An example of such an isocyanate is toluene diisocyanate (TDI). When polyfunctional isocyanates are used the reaction can be controlled to produce isocyanurate molecules themselves having additional isocyanate functionality e.g. as in the reaction.

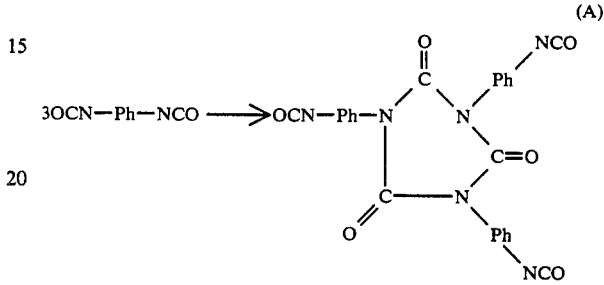

or under more vigorous conditions polyisocyanurates can be formed by further reaction of these intermediate units. In many cases it can be desirable to produce the isocyanaurate molecules, of which A is an example, for subsequent condensation with polyols, epoxides and the like.

The titanate compounds described herein also catalyse the formation of 2-oxazolidones from an isocyanate and an epoxide. Accordingly in a second aspect of the invention there is a process for the production of 2-oxazolidones from an isocyanate and an epoxide which process comprises reacting the isocyanate with the epoxide in the presence of a catalyst characterised in that the catalyst is a titanate compound of the type described herein.

By using simple monofunctional isocyanates and epoxides it is possible to prepare 2-oxazolidone molecules of reatively low molecular weight. However it is preferable to use polyfunctional isocyanates and polyfunctional epoxides in order to produce poly(2-oxazolidones). It will be obvious to those skilled in the art that, since the titanate catalyst catalyses the trimerisation of isocyanides to isocyanurates, in some cases the poly(2-oxazolidones) formed by the above reaction will contain a certain concentration of isocyanurate linkages. Such polymers which may for covenience be termed poly(2-oxazolidone/isocyanurate) are also contemplated herein.

In a final aspect of the invention there is provided a process for producing polyurethanes which also contain isocyanate and/or 2-oxazolidone linkages by reacting a polyfunctional isocyanide, a polyol and optionally a polyfunctional epoxide together in the presence of a catalyst characterised in that the catalyst is a titanate of the type described herein. In preparaing polyurethanes modified with isocyanurate and/or 2-oxazolidone linkages methods developed to prepare unmodified polyurethanes can be used. Such methods involve the addition of the titanate to the polyurethane forming reactant mix. The extent to which isocyanurate and/or oxazolidone linkages are produced in the polyurethane can be controlled by for example changing the concentration of the titanate catalyst in the polymerisation mixture or by adding the polyurethane partially polymerised. By careful adjustment of conditions it is possible to produce poly(urethane/isocyanurates) or poly(urethane/2-oxazolidone)s. or poly(urethane/isocyanurate/2-oxazolidones)2 over a wide compositional range, each material having specific physical properties.

All the polymeric materials described herein can be prepared in different physical forms by using methods of the art. Thus while the polymers may be made in the form of fibres, elastomers, resins, adhesives etc all the polymers described herein may be prepared in foam form by addition of a blowing agent, for example water, during the polymerisation.

All the reactions described in this document, whether generating low molecular weight species or polymeric materials, can be carried out at room temperature although higher temperatures may be used to accelerate the reaction if desired. The catalysts are typically added in amounts such that they constitute less than 10% by weight of the reactants.

The invention will now be illustrated by the following Examples.

PREPARATION OF THE TITANATE CATALYSTS

Examples 1-13

A distillation flask was charged with 0.1 moles of titanium isopropoxide and 0.4 moles of the appropriate alcohol (See Table 1). The flask was then flushed with dry nitrogen gas in order to remove any air and residual moisture. As soon as this was complete, the flask was warmed to the boiling point of isopropanol and isopropanol removed overhead by distillation. As soon as isopropanol distillation was complete the flask was cooled, the titanate catalyst removed and stored under dry nitrogen. The physical state of the catalyst in each particular case is given in the Table 1.

PREPARATION OF ISOCYANURATES USING THE TITANIUM CATALYSTS

Examples 14 to 22 illustrate that the novel catalysts described herein are able to catalyse the trimerisation of isocyanates to isocyanurates 10% by volume of the titanate catalyst was added to a test-tube carrying the isocyanate, in this case TDI 80/20 (TDI=toluene diisocyanates), and the gel time measured. All the catalysts produced polyisocyanurate gels at room temperature within a minute of mixing (Table 2.)

FORMATION OF FLEXIBLE URETHANE ISOCYANURATE FOAMS

Examples 23-25

Flexible poly(urethane/isocyanurate) foams were prepared using the standard formulation shown below but using a catalyst in a variety of solvents (1 g of a 50:50 wt mixture of catalyst and alcohol). In each case, the formulation produced a flexible poly(urethane/isocyanurate) foam containing isocyanurate linkages, as demonstrated by infrared spectroscopy.

| Formulation (excluding catalyst) | |
|---|---|
| Niax 11-34 (polyol) | 50 g |
| Water | 1.25 g |
| Ti(OCH$_2$CH$_2$N(CH$_3$)$_2$)$_4$ | 0.5 g |
| SC 193 (silicone surfactant) | 0.5 g |
| TDI 80/20 | 20.9 g |
| Example | 23 24 25 |

| Formulation (excluding catalyst) | | | |
|---|---|---|---|
| Alcohol | CH$_3$OH | C$_4$H$_9$OH | TEG |
| Cream Time (secs) | 17 | 16 | 18 |
| Rise Time secs | 185 | 190 | 200 |
| Density of foam kgm$^{-3}$ | 50.8 | 76.3 | 74.6 |

TEG = triethylene glycol

Example 26

1,4-Butanediol titanate (Ti(OC$_4$H$_8$OH)$_4$) was dissolved in triethylenglycol at a weight ratio of 1:4. 30 g of this solution, 2 g of silicone surfactant DC-193 and 20 g of fluorocarbon 11 were mixed to form a solution. Into this solution was charged 100 g of PAPI-35 (a polymeric isocyanate produced by the Upjohn Company) and vigorous agaitation applied.

The cream time and rise time for the mixture were respectively 30 and 45 seconds. The isocyanurate foam produced had a density of 33 kgm$^{-3}$ and the Butter Chimmey test result was found to be 70.6 percent weight retention.

Example 27

A poly(2-oxazolidone/isocyanurate) foam was prepared using the following formulation.

A premix was prepared by blending 26 g of DER-332 (the diglycidyl ether of Bisphenol A), 30 g of CCl$_3$F, 2 g of silicone surfactant DC-193 and 6 g of the catalyst Ti(OC$_2$H$_4$N(CH$_3$)$_2$)$_4$. Into this mixture was added 100 g of PAPI 135 isocuyanate. The final mixture was stirred vigorously until a foam was produced. In this experiment the cream time of the mix was 20 seconds and the rise time 158 seconds. The foam density was 28.5 Kgm$^{-3}$, the Butter Chimney Test showed 89.3% weight retention and the tumbling friability for 10 minutes was found to be 58.2%.

Example 28

This example illustrates the preparation of a TDI-based oxazolidone foam.

| Formulation | |
|---|---|
| DER 332 | 33.3 g |
| DC-193 | 1.0 g |
| CCl$_3$F | 5.0 g |
| TDI | 16.7 g |
| Ti(OC$_2$H$_4$N(CH$_3$)$_2$)$_4$ | 5.0 g |
| Rise time of mixture = 20 secs | |
| Density of foam product = 26.2 Kgm$^{-3}$ | |
| DER = Diglycidyl ether of bisphenol A | |

Example 29

A poly(oxazolidone/isocyanurate/urethane) elastomer was prepared as follows.

17.3 g of DER-332, 67.4 g of an isocyanate terminated urethane prepolymer and 2 g of Ti-(OCH$_2$CH$_2$N(CH$_3$)$_2$)$_4$ were mixed at room temperature. The prepolymer was prepared by reacting TDI 80/20 and Pluracol P-1010 (a polyether diol having a M.W. of 1000) at a NCO/OH equivalent ratio of 2:1. The blended mixture was solidified at room temperature and cured for 2 hours at 100° C. TGA data showed 10% decomposition at 353° C. and 40% at 402° C. Infrared spectroscopy showed the presence of both isocyanurate and oxazolidone linkages in the elastomer.

TABLE 1
PREPARATION OF TITANATE CATALYSTS

| Example | Alcohol | State of Product |
|---|---|---|
| 1 | Ethylene glycol | solid |
| 2 | Diethylene glycol | paste-like |
| 3 | Triethylene glycol | low viscous liquid |
| 4 | 1,2-Propanediol | solid |
| 5 | 1,4-Butanediol | highly viscous liquid |
| 6 | 2-Ethyl-1,3-hexanediol | viscous liquid |
| 7 | Methyldiethanolamine | needle crystal |
| 8 | Carbowax 600 | paste-like substance |
| 9 | Dantocol DHE* | solid |
| 10 | Dantocol DHE-5* | viscous liquid |
| 11 | Dantocol DHE-20* | viscous liquid |
| 12 | 1-Octanol | low viscous liquid |
| 13 | N,N—Dimethylethanolamine | low viscous liquid |

*Dantocol is a Hydantoin/alkylene oxide adduct.

TABLE 2
REACTIVITY OF TIANATES WITH TDI 80/20 (GEL TIME)

| Example | Parent alcohol of titane ester | Gel Time at Room Temp. | Gel Time at 80° C. |
|---|---|---|---|
| 14 | Carbowax 600 | 30–60 sec. | — |
| 15 | Dantocol DHE 5 | 20–30 min. | 5 min. |
| 16 | Dantocol DHE 20 | greater than 30 min. | — |
| 17 | Butanediol | 30–60 sec. | — |
| 18 | Triethylene Glycol | less than 30 sec. | — |
| 19 | 2-Ethyl,1,3-hexanediol | greater than 30 min. | 20 min. |
| 20 | 1-Octanol | greater than 30 min. | — |
| 21 | N,N—Diethylethanolamine | 1 min. | — |
| 22 | Titanium isopropoxide | instantaneous | — |

I claim:

1. Titanium compounds characterised in that the compounds are titanates of the formula $$Ti(OX)_4$$

or

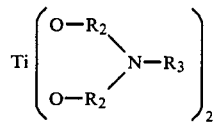

wherein (a) X is a group selected from the group comprising
—$R_1$, —$R_2$—OH, —($R_2$—O)$_n$—OH, —$R_2N(R_3)_2$
and —$R_2$—N($R_2$)($R_3$)OH
and (b) $R_1$ is a $C_5$-$C_8$ alkyl group
$R_2$ is a $C_2$-$C_4$ alkylene group
$R_3$ is either —$CH_3$ or —$CH_2CH_3$ 2. A process for the production of a titanium compound claimed in claim 1 wherein a lower alkyl titanate is contacted with an alcohol of formula XOH or (HO—$R_2$)$_2$N$R_3$ at elevated temperature and the alcohol derived from the alkyl titanate is removed by distillation.

3. A process for the production of a polyurethane containing isocyanurate and or 2-oxazolidone linkages by reacting a polyfunctional isocyanate, a polyol and/or a polyfunctional epoxide in the presence of, as catalyst, an effective amount of a titanium compound as claimed in claim 1.

4. A process for the production of an isocyanurate which process comprises reacting an isocyanate or mixture of isocyanates in the presence of, as catalyst, an effective amount of a titanium compound claimed in claim 1.

5. A process as claimed in claim 4 wherein the isocyanurate is a polyisocyanurate and the isocyanate is a polyfunctional isocyanate.

6. A process for the production of a 2-oxazolidone which process comprises reacting an isocyanate with an epoxide in the presence of, as catalyst, an effective amount of a titanium compound claimed in claim 1.

7. A process as claimed in claim 6 wherein the 2-oxazolidone is a poly(2-oxazolidone) and is formed from a polyfunctional isocyanate and a polyfunctional epoxide.

8. A process as claimed in claim 7 wherein the poly(2-oxazolidone) is a poly(2-oxazolidone/isocyanurate).

9. A process as claimed in claim 8 wherein the poly(2-oxazolidone/isocyanurate) is prepared in the presence of a blowing agent so as to obtain a foam.

10. A process as claimed in claim 3 wherein the polyurethane is prepared in the presence of a blowing agent so as to obtain a flexible foam or is prepared in the absence of a blowing agent so as to obtain an elastomer.

11. A polyurethane polymer whenever prepared by the process as defined in claim 3.